United States Patent
Kuzma et al.

(10) Patent No.: US 7,006,875 B1
(45) Date of Patent: Feb. 28, 2006

(54) CURVED PADDLE ELECTRODE FOR USE WITH A NEUROSTIMULATOR

(75) Inventors: Janusz A. Kuzma, Parker, CO (US); Todd K. Whitehurst, Santa Clarita, CA (US)

(73) Assignee: Advanced Bionics Corporation, Valencia, CA (US)

(*) Notice: Subject to any disclaimer, the term of this patent is extended or adjusted under 35 U.S.C. 154(b) by 121 days.

(21) Appl. No.: 10/809,747

(22) Filed: Mar. 25, 2004

Related U.S. Application Data

(60) Provisional application No. 60/458,071, filed on Mar. 26, 2003.

(51) Int. Cl.
*A61N 1/05* (2006.01)

(52) U.S. Cl. .................. 607/118; 607/115; 600/372; 600/373

(58) Field of Classification Search ............... 607/118, 607/142, 152, 132, 115, 129; 600/372, 373, 600/377, 381, 382, 386
See application file for complete search history.

(56) References Cited

U.S. PATENT DOCUMENTS

| | | |
|---|---|---|
| 4,649,936 A | 3/1987 | Ungar et al. |
| 5,193,539 A | 3/1993 | Schulman et al. |
| 5,193,540 A | 3/1993 | Schulman et al. |
| 5,344,438 A | 9/1994 | Testerman et al. |
| 5,505,201 A | 4/1996 | Grill, Jr. et al. |
| 5,964,702 A | 10/1999 | Grill, Jr. et al. |
| 6,051,017 A | 4/2000 | Loeb et al. |
| 6,185,452 B1 | 2/2001 | Schulman et al. |
| 6,308,105 B1 | 10/2001 | Duysens et al. |
| 6,738,672 B1 | 5/2004 | Schulman et al. |
| 2002/0193859 A1 | 12/2002 | Schulman et al. |

FOREIGN PATENT DOCUMENTS

| | | |
|---|---|---|
| WO | WO 98/43700 | 10/1998 |
| WO | WO 98/43701 | 10/1998 |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Whitehurst, et al. inventors for AB-203U; U.S. Appl. No. 10/178,011; filed Jun. 20, 2002; entitled "Implantable Microstimulators with Programmable Multielectrode Configuration and Uses Thereof".

Kuzma inventor for AB-057U1; U.S. Appl. No. 10/188,465; filed Jul. 2, 2002; entitled "Implantable Microdevice with Extended Lead and Remote Secondary Coil".

*Primary Examiner*—Robert E. Pezzuto
*Assistant Examiner*—Brian T. Gedeon
(74) *Attorney, Agent, or Firm*—Bryant R. Gold

(57) ABSTRACT

A curved paddle electrode allows the electrode to be placed over a relatively flat or oval shaped nerve bundle attached to fascia tissue without having to separate the nerve bundle from the fascia tissue. The electrode includes at least one suture hole that allows the electrode to be held in place over the nerve bundle through a clip-on stitch, or equivalent. In one embodiment, the curved paddle electrode provides a tripolar electrode configuration that allows three spaced-apart parallel electrode contacts to be positioned transverse to a target nerve bundle. Such electrode configuration allows bipolar or tripolar stimulation to occur. Other embodiments employ less or more than three electrode contacts. A preferred application of the curved paddle electrode is for the treatment of erectile dysfunction (ED), where the electrode is placed over the neurovascular bundle attached to the rectal fascia tissue near the rectum.

15 Claims, 2 Drawing Sheets

CURVED PADDLE ELECTRODE FOR USE WITH A NEUROSTIMULATOR

The present application claims the benefit of U.S. Provisional Patent Application Ser. No. 60/458,071, filed Mar. 26, 2003, which application is incorporated herein by reference.

BACKGROUND OF THE INVENTION

The present invention relates to cuff electrodes, and more particularly to a curved paddle electrode that may be used with a neurostimulator in order to efficiently apply electrical stimulation to desired nerve fibers or bundles.

A neurostimulator is a device that provides electrical stimulation to selected nerves throughout the body. One type of neurostimulator that has been developed in recent years by Advanced Bionics Corporation of Sylmar, Calif., is a tiny microstimulator known as a BION® microstimulator. Various embodiments and features of such BION microstimulator are disclosed, e.g., in U.S. Pat. Nos. 5,324,316; 5,405,367; 6,051,017, 6,185,452; and in PCT Publications WO 98/43700 and WO 98/43701, each of which patents or publications are incorporated herein by reference.

A microstimulator may be implanted via a small incision and/or via endoscopic means. In one preferred embodiment, the microstimulator is leadless, having electrodes fashioned or formed into its case. In such embodiment, the microstimulator must be implanted next to the nerve or tissue that is to be stimulated. Due to the small size of the microstimulator, such positioning is often possible, and allows desired neurostimulation to occur through minimally invasive surgery.

In other applications, however, it is not possible to implant the microstimulator right next to the nerve or tissue to be stimulated. In such instances, a leaded BION microstimulator of the type shown in applicant's co-pending U.S. patent application Ser. No. 10/188,465, filed 2 Jul. 2002 or U.S. patent application Ser. No. 10/178,011, filed 20 Jun. 2002, may be used. Both of these patent applications are incorporated herein by reference.

When a leaded BION microstimulator is used, an appropriate connection is used to connect the lead to the microstimulator. Such connection may be a detachable connection, as disclosed, e.g., in patent publication U.S. 2002/0193859 A1, also incorporated herein by reference; or a hard-wired connection, as shown, e.g., in the '465 patent application, referenced above.

The manner of connecting a lead to the BION microstimulator, or other neurostimulator, does not form part of the present invention. Rather, the present invention deals with the type of electrode that may be used at the distal end of such neurostimulator lead. The type of electrode used at the distal end of a neurostimulator lead plays a significant role in the effectiveness of the stimulation which is applied through the electrode to the nerve fibers or tissue.

One type of electrode known in the art is a cuff electrode. A cuff electrode encircles a targeted nerve fiber or bundle and offers the advantage of being effectively attached to the target fiber or bundle, thereby preventing the electrode from inadvertently moving away from its desired target. Representative types of cuff electrodes are illustrated in FIGS. 2B, 3A, 3B and 3C of the '465 patent application, previously incorporated herein by reference.

Disadvantageously, cuff electrodes do not always lend themselves to easy attachment to a targeted nerve fiber or bundle. That is, in some instances, the target nerve fiber or bundle, due to its position within the body, is not easily encircled without difficult surgery or without inflicting damage to the surrounding tissue or nerve bundle. For example, sometimes the target nerve bundle is attached along one side to fascia tissue, and there is no way to encircle the nerve bundle without pulling the nerve bundle apart or pulling it away from the fascia tissue. In such instances, there is a need for an electrode that can be attached to the targeted nerve fiber or bundle without encircling it and without inflicting damage to the surrounding tissue.

One type of electrode known in the art is a half-cuff electrode, as shown, e.g., in U.S. Pat. No. 5,344,438, incorporated herein by reference. However, such half-cuff electrode is not adapted to readily fit over a nerve bundle without dislodging the nerve bundle from the fascia tissue to which one side of the nerve bundle is connected. Thus, a need remains in the art for an electrode that can readily fit over a nerve bundle that is attached on one side to surrounding fascia tissue.

SUMMARY OF THE INVENTION

The present invention addresses the above and other needs by providing a curved paddle or semi-cuff electrode having a suture means that allows the electrode to be placed over a target nerve bundle and held in place through the suturing means.

In accordance with one aspect of the invention, the curved paddle or semi-cuff electrode provides a tripolar electrode configuration that allows three electrodes to be positioned transverse to a target nerve bundle. Such electrodes may each be connected to a separate wire within the lead, or two of the electrodes may be connected to the same wire within the lead.

In accordance with another aspect of the invention, the curved paddle or semi-cuff electrode is particularly adapted to be used to stimulate a neurovascular bundle near the rectal fascia for the purpose of treating Erectile Dysfunction (ED).

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
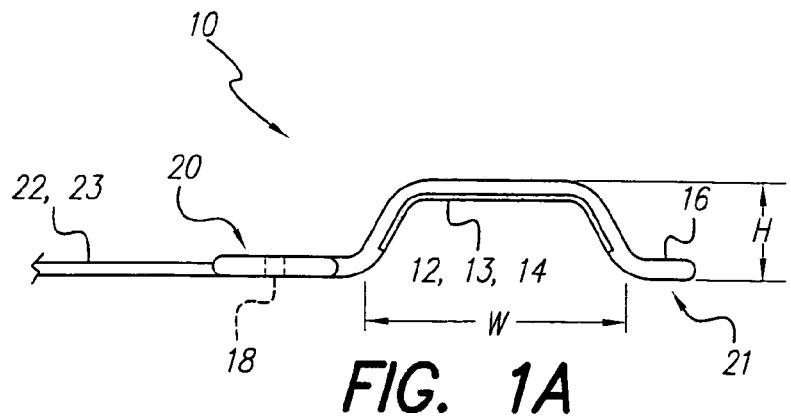
FIG. 1A is side view of a semi-cuff or curved paddle electrode made in accordance with the present invention.
Figure 1B:
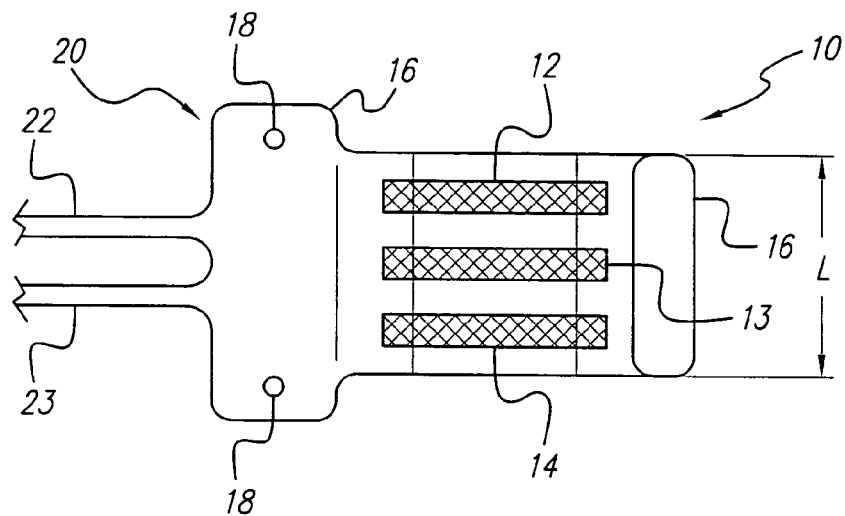
FIG. 1B is a bottom view of the electrode of FIG. 1A.
Figure 1C:
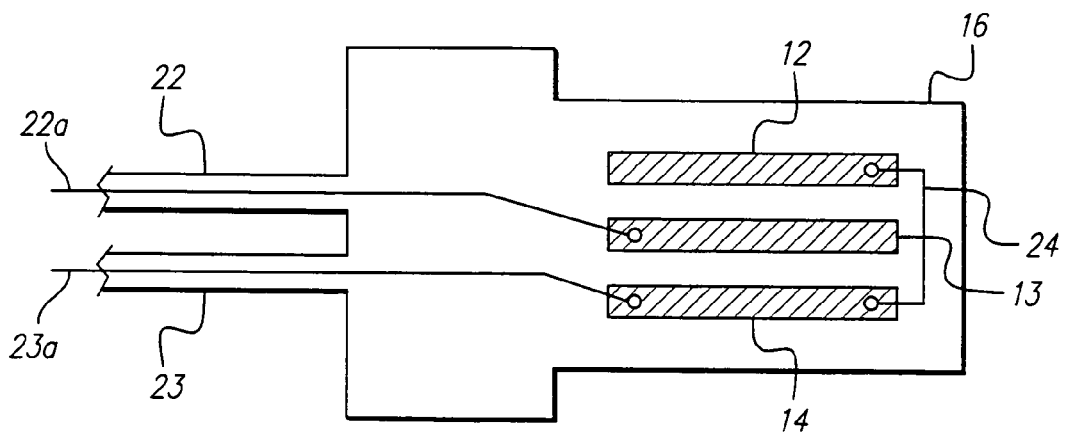
FIG. 1C shows the connections to the electrode contacts of the electrode of FIG. 1A.

FIGS. 1A, 1B and 1C illustrate a preferred embodiment of a curved paddle electrode 10 made in accordance with the present invention. As seen in these figures, three electrode contacts 12, 13 and 14, are carried in a spaced-apart parallel relationship on a non-conductive carrier 16. The electrode contacts 12, 13 and 14 are made from any suitable body-compatible metal, such as platinum or its alloys. The carrier 16 is made from any suitable body-compatible non-conductive material, such as silicone or Silastic or similar materials.

Inasmuch as many patients who use an electrode 10 may have to undergo an MRI investigation, it is also preferred that the materials used to make the electrode 10 be MRI compatible. This means that the electrode should not create a "shadow" that limits the value of the MRI.

As seen best in FIG. 1A, the carrier 16 is formed in "C" shape, with the electrode contacts 12, 13 and 14 being placed in their parallel spaced-apart relationship on the inside of the "C". A distal portion 21 of the carrier 16, as well as a proximal portion 20 of the carrier 16, are relatively flat, providing surfaces which may lie against the fascia tissue to which the nerve bundle is attached and over which the curved paddle electrode is placed, as described more fully below. The form or shape of the electrode 10 may be maintained, in large part, by the electrode contacts 12, 13 and 14. That is, during the manufacturing process, the electrode contacts may be bent and formed over a relatively flat or oval shape mold, and wires may be attached, e.g., welded, thereto. The carrier 16 may then be molded over the electrode contacts and wires and allowed to cure. Depending upon the ability of the electrode contacts to bend, the resulting electrode may thus be somewhat malleable.

One or more lead wires 22a, 23a attach to a proximal end 20 of the electrode 10. As shown in FIGS. 1B and 1C, such lead wires may be carried in respective leads 22 and 23. However, it is also to be understood, that a single lead may attach to the proximal end 20 of the electrode 10 and carry multiple wires 22a, 23a.

A preferred electrode configuration is a tripolar configuration, as illustrated in FIG. 1C. As seen in FIG. 1C, wire 22a connects to electrode contact 13, in the center of the electrode array; while wire 23a connects to electrode contact 14, on one side of the array. Another wire 24 then connects electrode contact 14 to electrode contact 12. Hence, in this configuration, the side electrode contacts 12 and 14 are electrically connected to wire 23a, and the center electrode contact 13 is connected to wire 22a. The microstimulator (not shown), or other neurostimulator to which the wires 22a and 23a are attached, may then apply an electrical stimulus through the electrode contacts 12, 13 and 14.

Other embodiments may employ a separate wire attached to each electrode contact 12, 13 and 14, so that electrical stimuli may be applied between any combination of the electrode contacts.

While one preferred embodiment employs three parallel spaced-apart electrode contacts, as shown, e.g., in FIG. 1B, it is to be noted that different numbers of electrode contacts may be used. Another embodiment of the curved paddle electrode 10, for example, may employ more than three electrode contacts, e.g., four or more electrode contacts. A further embodiment of the electrode 10 employs only one electrode contact. Another embodiment employs two parallel spaced-apart electrode contacts.

The number and spacing of the electrode contacts is not arbitrary nor a mere design choice. Rather, the application for which the curved paddle electrode 10 is to be used, including the size and location of the nerve to be covered by the electrode, will dictate in large part the number of electrode contacts and their relative size and spacing.

A proximal end portion 20 of the electrode 10 includes at least one suture hole 18. As shown best in FIG. 1B, two suture holes 18 are provided, on opposite sides of the proximal end portion 20 of the electrode carrier 16. As is explained in more detail below, a suture may be fastened in these holes and connected with adjacent fascia tissue in order to hold the electrode 10 in position over a desired nerve bundle.

Figure 2:
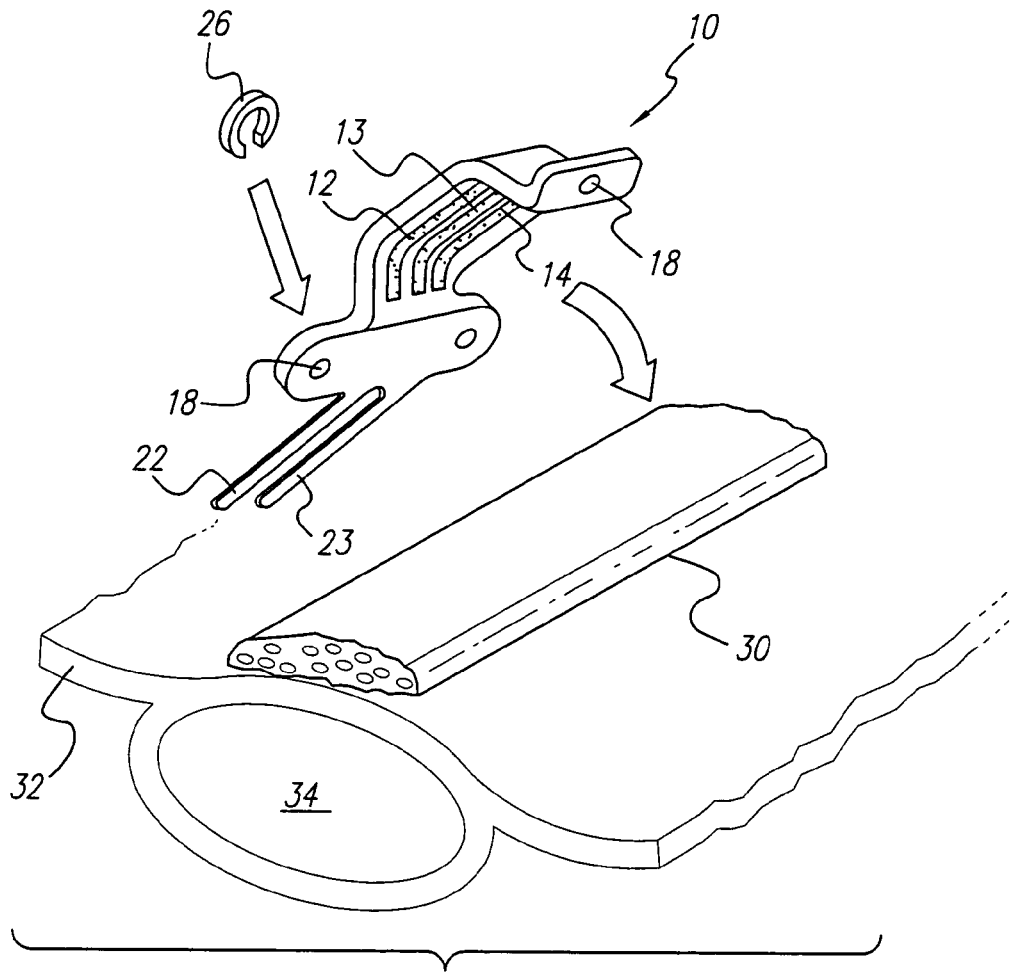
FIG. 2 is an exploded view that illustrates use of the semi-cuff or curved paddle electrode of the present invention in order to stimulate a nerve bundle near the rectal facia.
Figure 3:
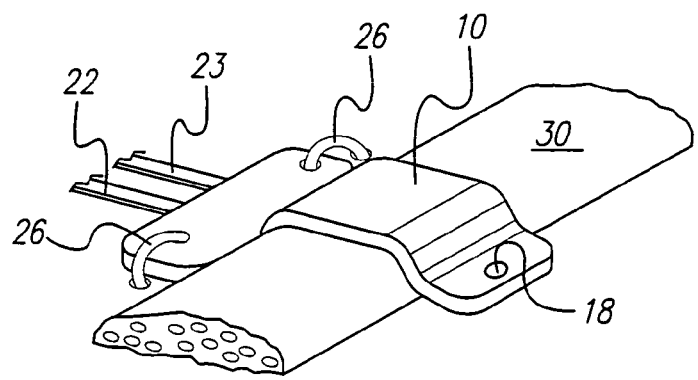
FIG. 3 shows the electrode of FIG. 2 sutured in place over the nerve bundle.

Turning next to FIGS. 2 and 3, the manner of placing and holding the curved paddle electrode 10 over a target nerve bundle 30 is illustrated. One preferred application for the electrode 10 is for the treatment of ED. In such instance, the target nerve bundle 30 is relatively flat or oval in shape, and is about 1 cm in width. It is best if this nerve bundle not be disconnected from the rectal fascia 32 to which the bundle 30 is attached in the vicinity of the rectum 34. Thus, the preferred approach for attaching the electrode 10 is to place it over the nerve bundle 30, with the nerve bundle 30 passing through the center of the "C" shaped electrode, and with the electrode contacts 12, 13 and 14 being placed next to and in contact with the nerve bundle 30.

Once the curved paddle electrode 10 has been placed over the nerve bundle 30, it is sutured in place using, e.g, a clip-on stitch 26. Once sutured using this or an equivalent manner through the suture holes 18, the electrode contacts 12, 13 and 14 of the electrode 10 are held in a transverse position over and around the nerve bundle 30, as seen best in FIG. 3, and are maintained in this position by the clip-on stitches 26, or equivalent.

As shown in FIGS. 2 and 3, an additional suture hole 18 may be provided near a distal end of the carrier 16. This suture hole need not be used, but is available for use if the surgeon feels a need to use it to better secure the electrode over the desired nerve bundle. Alternatively, the material from which the carrier 16 is made, particularly the material at the distal flat portion 21 and proximal flat portion 20 (see FIG. 1A), may be puncturable or pierced by a sharp needle or other suturing tool, e.g., a suture clip, thereby allowing suturing to occur even without the presence of suture holes 18. As needed, reinforcing ridges may be molded around the area that is to be punctured with the suturing tool, thereby preventing the flat portions of the carrier 16 from tearing once a puncture has been made.

For an Erectile Dysfunction (ED) application, the electrode will generally be implanted at the end of a prostatectomy, e.g., as part of the same procedure. The neurovascular bundle 30 may be accessed laparoscopically. It is felt that a large percentage of ED patients who have to undergo a prostatectomy would likely be willing to be implanted with the electrode lead, since it may be done as part of the same prostatectomy procedure.

Advantageously, the electrode array 10 with relatively flat distal portion 16 and relatively flat proximal portion 20 fits nicely over the neurovascular bundle 30, and may be sutured on one or both sides to the rectal fascia 32. There need be no concerns about constriction, since the underlying tissue (rectum) is also soft.

Further, as required, the curved paddle electrode may be made available in a kit that includes different sizes of the electrode, e.g., primarily different widths, W, and different heights, H, (see FIG. 1A for definitions of W and H) to fit over different sized nerve bundles. The length L (see FIG. 1B) may also be varied (but L will primarily vary as a function of the number of electrode contacts that are used, not based on the size of the nerve bundle). During the implant procedure, the surgeon can (using an appropriate tool) measure the approximate size (height and width) of the nerve bundle, and then select the electrode from the kit that best fits the nerve bundle over which it is to be placed so as to position the electrode contacts against the nerve bundle but without undue pressure that might cause constriction of the nerve bundle.

In operation, when the nerve bundle 30 is stimulated, a neurotransmitter (Nitric Oxide, NO) is released at the level of the synapse. As a result of this release in the cell, GMP (guanylic acid) is turned into a cGMP. Such biochemistry results in an erection. The cGMP is turned back into GMP with Phosphodiesterase 3, which is naturally found in the body. (By way of comparison, a popular drug for treating ED, Viagra®, is an inhibitor of Phosphodiesterase 3.)

While the invention herein disclosed has been described by means of specific embodiments and applications thereof, numerous modifications and variations could be made thereto by those skilled in the art without departing from the scope of the invention set forth in the claims.

What is claimed is:

1. An implantable electrode adapted for placement over a relatively flat or oval nerve bundle that remains attached to fascia tissue, comprising:
    a "C"-shaped non-conductive carrier adapted to fit over the nerve bundle while it remains attached to fascia tissue, the C-shaped portion having a distal portion and a proximal portion that are relatively flat, providing surfaces which are adapted to lie against the fascia tissue to which the nerve bundle is attached;
    at least one electrode contact carried on an inside surface of the "C"-shaped carrier; and
    at least one wire connected to the electrode contact;
    wherein the at least one wire exits the "C"-shaped carrier along a proximal portion thereof; and
    wherein the at least one wire is carried in an insulating lead.

2. The electrode of claim 1 wherein the relatively flat proximal portion of the electrode includes at least one suture hole through which a suture stitch may be placed to connect the proximal portion of the electrode to the surrounding fascia tissue.

3. The electrode of claim 2 wherein the relatively flat distal portion of the electrode includes a suture hole through which a suture stitch may be placed to connect the distal portion of the electrode to the surrounding fascia tissue.

4. The electrode of claim 1 wherein there are at least two parallel spaced-apart electrode contacts carried on the inside surface of the "C"-shaped carrier.

5. The electrode of claim 3 wherein there are at least three parallel spaced-apart electrode contacts carried on the inside surface of the "C"-shaped carrier.

6. The electrode of claim 5 wherein two of the three electrode contacts are electrically connected together.

7. The electrode of claim 6 wherein the two electrode contacts that are electrically connected together reside on the outside of a center electrode contact.

8. The electrode of claim 5 wherein the at least three parallel spaced-apart electrode contacts are embedded within the carrier, with one surface of the electrode contacts being exposed on the inside surface of the "C"-shaped carrier.

9. A curved paddle electrode (10) adapted to fit over a nerve bundle (30) without dislodging the nerve bundle from fascia tissue (32) to which one side of the nerve bundle is connected, comprising:
    a non-conductive carrier (16) adapted to fit over the nerve bundle, the non-conductive carrier having a distal portion and a proximal portion that are substantially flat;
    at least three parallel spaced-apart electrode contact strips (12, 13, 14) carried on the non-conductive carrier (16), wherein two of the three electrode contact strips are electrically connected to each other;
    at least one wire (23a) that connects to the two spaced-apart electrode contacts that are electrically connected to each other; and
    at least one wire (22a) that connects to the electrode contact not connected to any other electrode contacts;
    wherein the non-conductive carrier (16) is adapted to fit over the nerve bundle (30) so that the spaced-apart electrode contact strips are positioned substantially transverse to the nerve bundle so as to make physical contact therewith.

10. The electrode of claim 9 wherein the electrode contact strip (13) that is not electrically connected to another electrode contact strip is in the middle of the two electrode contact strips (12, 14) that are electrically connected to each other.

11. The electrode of claim 6 further including means for suturing the electrode to the fascia tissue.

12. The electrode of claim 11 wherein the means for suturing the electrode to the fascia tissue comprises at least one suture hole in at least one of the proximal or distal flat portions of the carrier.

13. The electrode of claim 11 wherein the means for suturing the electrode to the fascia tissue comprises a puncturable material within the proximal and distal flat portions of the carrier that may be punctured or pierced with a suturing instrument.

14. The electrode of claim 9 wherein the combination of the non-conductive carrier and the at least three spaced-apart electrode contact strips render the electrode malleable so that it can be bent and formed to a desired shape.

15. A kit of curved paddle electrodes adapted to be used with a neurostimulator, said kit comprising:
    a plurality of electrodes of different sizes, wherein each electrode within the kit comprises:
        a "C"-shaped non-conductive carrier adapted to fit over a nerve bundle while it remains attached to fascia tissue, the C-shaped portion having a height H, a width W, and a length L, and further having a distal portion and a proximal portion that are relatively flat, providing surfaces which are adapted to lie against fascia tissue to which the nerve bundle is attached,
        at least one electrode contact carried on an inside surface of the "C"-shaped carrier, and
        at least one wire connected to the electrode contact,
        wherein the at least one wire exits the "C"-shaped carrier along a proximal portion thereof, and
        wherein the at least one wire is carried in an insulating lead; and
    wherein the different sizes of the plurality of electrodes are determined by different heights H and widths W;
    whereby an electrode may be selected from the kit of electrodes that is adapted to best fit a given nerve bundle over which it is to be placed without undue pressure that might cause constriction of the nerve bundle.

* * * * *